US012213753B2

(12) United States Patent
Alden et al.

(10) Patent No.: US 12,213,753 B2
(45) Date of Patent: Feb. 4, 2025

(54) INDICATOR MECHANISM FOR AN ACTUATOR CONTROLLED SURGICAL INSTRUMENT

(71) Applicant: INTUITIVE SURGICAL OPERATIONS, INC., Sunnyvale, CA (US)

(72) Inventors: Donald Alden, Sunnyvale, CA (US); Bram Gilbert Antoon Lambrecht, Redwood City, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 238 days.

(21) Appl. No.: 17/726,773

(22) Filed: Apr. 22, 2022

(65) Prior Publication Data
US 2022/0354598 A1    Nov. 10, 2022

Related U.S. Application Data

(63) Continuation of application No. 16/680,194, filed on Nov. 11, 2019, now Pat. No. 11,344,378, which is a
(Continued)

(51) Int. Cl.
*A61B 34/30*    (2016.01)
*A61B 17/00*    (2006.01)
*A61B 90/00*    (2016.01)

(52) U.S. Cl.
CPC .... *A61B 34/30* (2016.02); *A61B 2017/00477* (2013.01); *A61B 2090/0803* (2016.02); *A61B 2090/0807* (2016.02)

(58) Field of Classification Search
CPC .......... A61B 34/30; A61B 2017/00477; A61B 2090/0803; A61B 2090/0807; A61B 34/37; A61B 90/08
See application file for complete search history.

(56) References Cited

U.S. PATENT DOCUMENTS 2,752,880 A * 7/1956 Jackson .................... G09F 7/00
                                                         116/323
4,592,498 A    6/1986 Braun et al.
(Continued)

FOREIGN PATENT DOCUMENTS

CN    101011273 A    8/2007
CN    101321606 A    12/2008
(Continued)

OTHER PUBLICATIONS

CN Office Action dated Jan. 28, 2022, in Application No. CN201910766785.6 with English Translation, 12 pages.
(Continued)

*Primary Examiner* — John Fitzgerald
*Assistant Examiner* — Tania Courson
(74) *Attorney, Agent, or Firm* — JONES ROBB, PLLC

(57) ABSTRACT

A method for providing a visual indication regarding a state of an instrument comprises sensing usage information about the instrument and using a motor to rotate an indicator body from a first position to a second position in response to sensing the usage information meets a predetermined condition. The method further comprises holding the indicator body in the first position or the second position, respectively. In the first position a first portion of the indicator body is visible on an exterior of the instrument and in the second position a second portion is visible. In the first position, the first portion of the indicator body provides a visual indication that the usage information of the instrument does not meet the predetermined condition, and in the second position the second portion of the visual indicator body provides a visual indication that the usage information of the instrument meets the predetermined condition.

19 Claims, 7 Drawing Sheets

Related U.S. Application Data continuation of application No. 15/121,366, filed as application No. PCT/US2015/020870 on Mar. 17, 2015, now Pat. No. 10,470,829.

(60) Provisional application No. 62/012,081, filed on Jun. 13, 2014, provisional application No. 61/954,453, filed on Mar. 17, 2014.

(56) References Cited

U.S. PATENT DOCUMENTS

| | | | |
|---|---|---|---|
| 4,606,343 | A | 8/1986 | Conta et al. |
| 4,619,391 | A | 10/1986 | Sharkany et al. |
| 4,951,860 | A | 8/1990 | Peters et al. |
| 5,313,935 | A | 5/1994 | Kortenbach et al. |
| 5,359,993 | A | 11/1994 | Slater et al. |
| 5,397,046 | A | 3/1995 | Savage et al. |
| 5,397,323 | A | 3/1995 | Taylor et al. |
| 5,630,431 | A | 5/1997 | Taylor |
| 5,766,126 | A | 6/1998 | Anderson |
| 5,991,355 | A | 11/1999 | Dahlke |
| 6,331,181 | B1 | 12/2001 | Tierney et al. |
| 6,468,265 | B1 | 10/2002 | Evans et al. |
| 6,601,748 | B1 | 8/2003 | Fung et al. |
| 7,477,927 | B2 | 1/2009 | Stoianovici et al. |
| 7,835,823 | B2 | 11/2010 | Sillman et al. |
| 8,241,271 | B2 | 8/2012 | Millman et al. |
| 8,939,894 | B2 | 1/2015 | Morrissette et al. |
| 9,283,043 | B2 | 3/2016 | Tsao et al. |
| 9,398,935 | B2 | 7/2016 | Kim et al. |
| 9,655,680 | B2 | 5/2017 | Shim et al. |
| 9,782,198 | B2 | 10/2017 | Elhawary et al. |
| 9,980,829 | B2 | 5/2018 | Miles et al. |
| 10,188,391 | B2 | 1/2019 | Viola et al. |
| 10,285,694 | B2 | 5/2019 | Viola et al. |
| 10,470,829 | B2 | 11/2019 | Alden et al. |
| 10,758,234 | B2* | 9/2020 | Malkowski .......... A61B 17/083 |
| 11,344,378 | B2 | 5/2022 | Alden et al. |
| 2002/0032451 | A1 | 3/2002 | Tierney et al. |
| 2005/0043718 | A1 | 2/2005 | Madhani et al. |
| 2007/0151389 | A1 | 7/2007 | Prisco et al. |
| 2008/0135600 | A1 | 6/2008 | Hiranuma et al. |
| 2008/0262654 | A1 | 10/2008 | Omori et al. |
| 2009/0071554 | A1 | 3/2009 | Beckman et al. |
| 2009/0099520 | A1 | 4/2009 | Millman et al. |
| 2009/0178609 | A1* | 7/2009 | Kreshek .................. G09F 11/23 116/308 |
| 2010/0163031 | A1* | 7/2010 | Morton ............. A61M 15/0076 116/316 |
| 2011/0137323 | A1 | 6/2011 | Malkowski et al. |
| 2012/0006252 | A1* | 1/2012 | Warner .................. G09F 11/23 116/284 |
| 2012/0143211 | A1 | 6/2012 | Kishi |
| 2013/0253480 | A1 | 9/2013 | Kimball et al. |
| 2014/0194699 | A1 | 7/2014 | Roh et al. |
| 2015/0338728 | A1 | 11/2015 | Amron |
| 2016/0354166 | A1 | 12/2016 | Popovic et al. |
| 2017/0007335 | A1 | 1/2017 | Popovic et al. |
| 2017/0165847 | A1 | 6/2017 | Popovic et al. |
| 2020/0078107 | A1 | 3/2020 | Alden et al. |
| 2023/0115444 | A1* | 4/2023 | Goodman .......... A61B 17/1285 227/175.1 |

FOREIGN PATENT DOCUMENTS

| | | |
|---|---|---|
| CN | 201281819 Y | 7/2009 |
| EP | 1790294 A1 | 5/2007 |
| EP | 2484304 A2 | 8/2012 |
| EP | 2659847 A1 | 11/2013 |
| JP | H08248838 A | 9/1996 |
| JP | 2006081687 A | 3/2006 |
| JP | 2006292805 A | 10/2006 |
| JP | 2011120908 A | 6/2011 |
| JP | 2012192103 A | 10/2012 |
| WO | WO-2008067143 A2 | 6/2008 |
| WO | WO-2009039058 A1 | 3/2009 |

OTHER PUBLICATIONS

Extended European Search Report for Application No. 15765163.9, mailed on Oct. 10, 2017, 10 pages.

Extended European Search Report for Application No. EP19212146.5 mailed on Jan. 20, 2020, 5 pages.

International Search Report and Written Opinion for Application No. PCT/US15/20870, mailed on Jun. 9, 2015, 20 pages.

Vertut, J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

\* cited by examiner

INDICATOR MECHANISM FOR AN ACTUATOR CONTROLLED SURGICAL INSTRUMENT

CROSS-REFERENCE TO RELATED APPLICATIONS

This application is a continuation application of application Ser. No. 16/680,194, filed Nov. 11, 2019, which is a continuation application of application Ser. No. 15/121,366, filed Aug. 24, 2016 (now U.S. Pat. No. 10,470,829), which is a U.S. national stage application under 35 U.S.C. § 371(c) of International Application No. PCT/US2015/020870 filed on Mar. 17, 2015 and claims priority to U.S. Provisional Application No. 62/012,081, filed Jun. 13, 2014 and U.S. Provisional Application No. 61/954,453, filed Mar. 17, 2014, each of which are incorporated herein by reference in their entirety and for all purposes.

FIELD

Embodiments of the invention relate to the field of indicators; and more specifically, to non-resettable indicators that display at least one of two states for use in actuator controlled surgical instruments.

BACKGROUND

Minimally invasive surgery (MIS) (e.g., endoscopy, laparoscopy, thoracoscopy, cystoscopy, and the like) allows a patient to be operated upon through small incisions by using elongated surgical instruments introduced to an internal surgical site. Generally, a cannula is inserted through the incision to provide an access port for the surgical instruments. The surgical site often comprises a body cavity, such as the patient's abdomen. The body cavity may optionally be distended using a clear fluid such as an insufflation gas. In traditional minimally invasive surgery, the surgeon manipulates the tissues by using hand-actuated end effectors of the elongated surgical instruments while viewing the surgical site on a video monitor.

The elongated surgical instruments will generally have an end effector in the form of a surgical tool such as a forceps, a scissors, a clamp, a needle grasper, or the like at one end of an elongate tube. The surgical tool is generally coupled to the elongate tube by one or more articulated sections to control the position and/or orientation of the surgical tool. An actuator that provides the actuating forces to control the articulated section is coupled to the other end of the elongate tube. A means of coupling the actuator forces to the articulated section runs through the elongate tube. Two actuators may be provided to control two articulated sections, such as an "arm" that positions the surgical tool and a "wrist" the orients and manipulates the surgical tool, with means for coupling both actuator forces running through the elongate tube.

It may desirable that the elongate tube be somewhat flexible to allow the surgical instrument to adapt to the geometry of the surgical access path. In some cases, the articulated sections provide access to a surgical site that is not directly in line with the surgical access port. It may be desirable to use cables as the means of coupling the actuator forces to the articulated sections because of the flexibility they provide and because of the ability of a cable to transmit a significant force, a substantial distance, through a small cross-section.

The cables may be operated at close to their maximum allowable loading to minimize the cross-section of cables and hence of the elongate tube. For this and other reasons, the number of uses of this type of surgical instrument may be limited.

In view of the above, it is desirable to provide an indicator that can show that a surgical instrument has expired and should be removed from inventory.

SUMMARY

A method for providing a visual expiration indication for a surgical instrument includes holding an indicator body in a first position with a detent mechanism to provide a visual in-service indication for the surgical instrument. The indicator body is engaged with a motor and the indicator body is rotated with the motor from the first position to a second position that provides a visual expired indication. The indicator body is prevented from rotating from the second position to the first position with the detent mechanism. The detent mechanism may hold the indicator body in one of only two positions. The visual indications may be displayed through an aperture fixed to the base of the surgical instrument. The indicator body may be elastically deformed when the indicator body is rotated from the first position to the second position. The motor may be rotated to gain momentum before rotating the indicator body.

A controller may track use events for a surgical instrument to determine expiration. Use events may include operations and conditions in addition to those that occur in the surgical instrument. When the use events tracked by the controller indicate expiration, the controller may rotate a motor to set the visual indication to expired.

Other features and advantages of the present invention will be apparent from the accompanying drawings and from the detailed description that follows below.

BRIEF DESCRIPTION OF THE DRAWINGS

The invention may best be understood by referring to the following description and accompanying drawings that are used to illustrate embodiments of the invention by way of example and not limitation. In the drawings, in which like reference numerals indicate similar elements.

DESCRIPTION OF EMBODIMENTS

In the following description, numerous specific details are set forth. However, it is understood that embodiments of the invention may be practiced without these specific details. In other instances, well-known circuits, structures and techniques have not been shown in detail in order not to obscure the understanding of this description.

In the following description, reference is made to the accompanying drawings, which illustrate several embodiments of the present invention. It is understood that other embodiments may be utilized, and mechanical compositional, structural, electrical, and operational changes may be made without departing from the spirit and scope of the present disclosure. The following detailed description is not to be taken in a limiting sense, and the scope of the embodiments of the present invention is defined only by the claims of the issued patent.

The terminology used herein is for the purpose of describing particular embodiments only and is not intended to be limiting of the invention. Spatially relative terms, such as "beneath", "below", "lower", "above", "upper", and the like may be used herein for ease of description to describe one element's or feature's relationship to another element(s) or feature(s) as illustrated in the figures. It will be understood that the spatially relative terms are intended to encompass different orientations of the device in use or operation in addition to the orientation depicted in the figures. For example, if the device in the figures is turned over, elements described as "below" or "beneath" other elements or features would then be oriented "above" the other elements or features. Thus, the exemplary term "below" can encompass both an orientation of above and below. The device may be otherwise oriented (e.g., rotated 90 degrees or at other orientations) and the spatially relative descriptors used herein interpreted accordingly.

As used herein, the singular forms "a", "an", and "the" are intended to include the plural forms as well, unless the context indicates otherwise. It will be further understood that the terms "comprises" and/or "comprising" specify the presence of stated features, steps, operations, elements, and/or components, but do not preclude the presence or addition of one or more other features, steps, operations, elements, components, and/or groups thereof.

Figure 1:
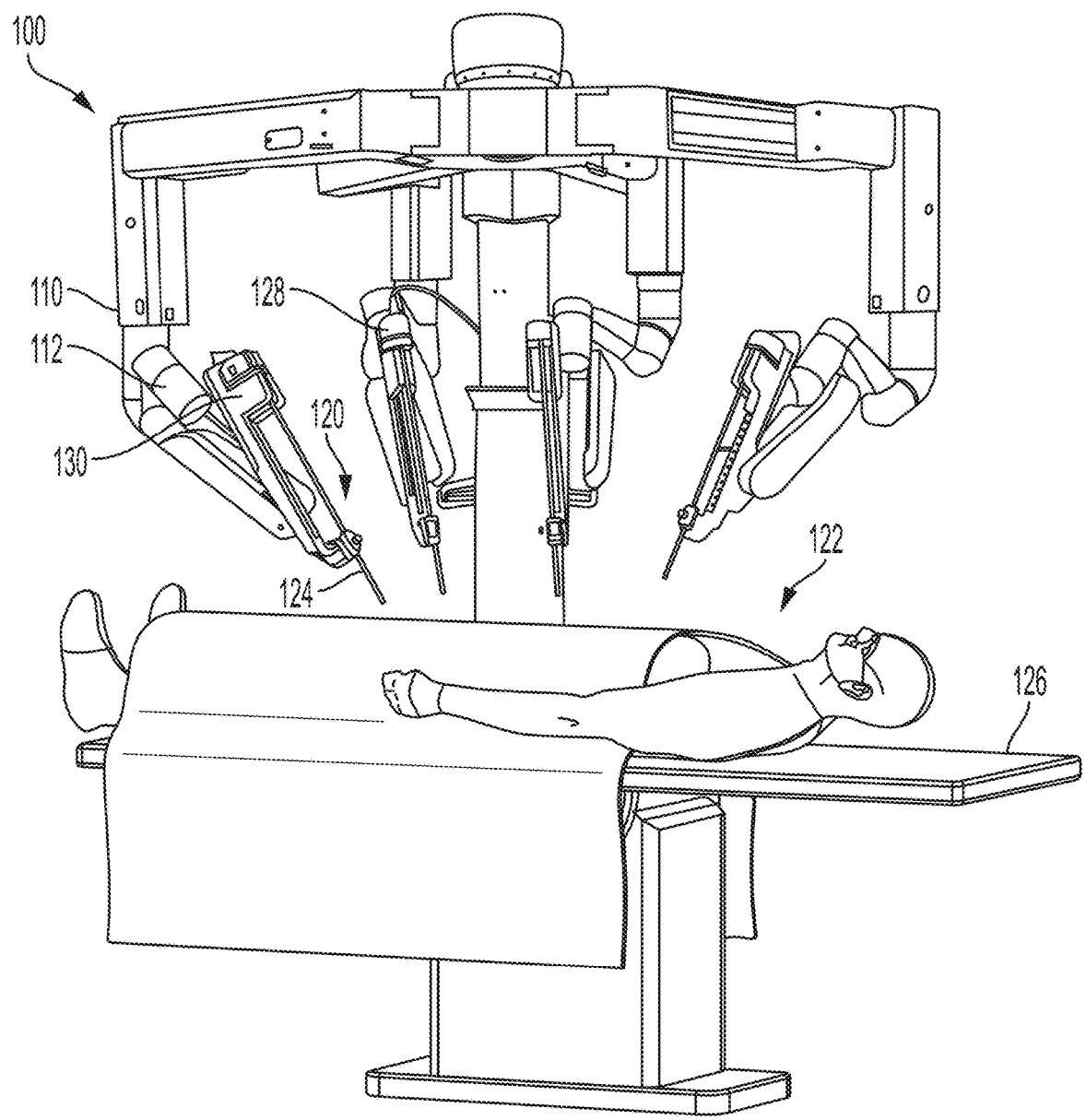
FIG. 1 is a simplified perspective view of a remotely operated surgical system with an actuator controlled surgical instrument inserted through a port in a patient's abdomen.

FIG. 1 is a view of an illustrative patient-side portion 100 of a teleoperated surgical system, in accordance with embodiments of the present invention. The patient-side portion 100 includes support assemblies 110 and one or more surgical instrument manipulators 112 at the end of each support assembly. The support assemblies optionally include one or more unpowered, lockable setup joints that are used to position the surgical instrument manipulator(s) 112 with reference to the patient for surgery. As depicted, the patient-side portion 100 rests on the floor. In other embodiments the patient-side portion may be mounted to a wall, to the ceiling, to the operating table 126, which also supports the patient's body 122, or to other operating room equipment. Further, while the patient-side portion 100 is shown as including four manipulators 112, more or fewer manipulators 112 may be used. Still further, the patient-side portion 100 may consist of a single assembly as shown, or it may include two or more separate assemblies, each optionally mounted in various possible ways.

Each surgical instrument manipulator 112 supports one or more surgical instruments 120 that operate at a surgical site within the patient's body 122. Each manipulator 112 may be provided in a variety of forms that allow the associated surgical instrument to move with one or more mechanical degrees of freedom (e.g., all six Cartesian degrees of freedom, five or fewer Cartesian degrees of freedom, etc.). Typically, mechanical or control constraints restrict each manipulator 112 to move its associated surgical instrument around a center of motion on the instrument that stays stationary with reference to the patient, and this center of motion is typically located to be at the position where the instrument enters the body.

The term "surgical instrument" is used herein to describe a medical device configured to be inserted into a patient's body and used to carry out surgical or diagnostic procedures. The surgical instrument typically includes an end effector associated with one or more surgical tasks, such as a forceps, a needle driver, a shears, a bipolar cauterizer, a tissue stabilizer or retractor, a clip applier, an anastomosis device, an imaging device (e.g., an endoscope or ultrasound probe), and the like. Some surgical instruments used with embodiments of the invention further provide an articulated support (sometimes referred to as a "wrist") for the end effector so that the position and orientation of the end effector can be manipulated with one or more mechanical degrees of freedom in relation to the instrument's shaft. Further, many surgical end effectors include a functional mechanical degree of freedom, such as jaws that open or close, or a knife that translates along a path. Surgical instruments may also contain stored (e.g., on a semiconductor memory inside the instrument) information that may be permanent or may be updatable by the surgical system. Accordingly, the system may provide for either one-way or two-way information communication between the instrument and one or more system components.

A functional teleoperated surgical system will generally include a vision system portion (not shown) that enables the operator to view the surgical site from outside the patient's body 122. The vision system typically includes a surgical instrument that has a video-image-capture function 128 (a "camera instrument") and one or more video displays for displaying the captured images. In some surgical system configurations, the camera instrument 128 includes optics that transfer the images from the distal end of the camera instrument 128 to one or more imaging sensors (e.g., CCD or CMOS sensors) outside of the patient's body 122. Alternatively, the imaging sensor(s) may be positioned at the distal end of the camera instrument 128, and the signals produced by the sensor(s) may be transmitted along a lead or wirelessly for processing and display on the video display. An illustrative video display is the stereoscopic display on the surgeon's console in surgical systems commercialized by Intuitive Surgical, Inc., Sunnyvale, Calif.

A functional teleoperated surgical system will further include a control system portion (not shown) for controlling the movement of the surgical instruments 120 while the instruments are inside the patient. The control system portion may be at a single location in the surgical system, or it may be distributed at two or more locations in the system (e.g., control system portion components may be in the system's patient-side portion 100, in a dedicated system control console, or in a separate equipment rack). The teleoperated master/slave control may be done in a variety of ways, depending on the degree of control desired, the size of the surgical assembly being controlled, and other factors. In some embodiments, the control system portion includes one or more manually-operated input devices, such as a joystick, exoskeletal glove, a powered and gravity-compensated manipulator, or the like. These input devices control teleoperated motors which, in turn, control the movement of the surgical instrument.

The forces generated by the teleoperated motors are transferred via drivetrain mechanisms, which transmit the forces from the teleoperated motors to the surgical instrument 120. In some telesurgical embodiments, the input devices that control the manipulator(s) may be provided at a location remote from the patient, either inside or outside the room in which the patient is placed. The input signals from the input devices are then transmitted to the control system portion. Persons familiar with telemanipulative, teleoperative, and telepresence surgery will know of such systems and their components, such as the da Vinci® Surgical System commercialized by Intuitive Surgical, Inc. and the Zeus® Surgical System originally manufactured by Computer Motion, Inc., and various illustrative components of such systems.

As shown, both the surgical instrument 120 and an optional entry guide 124 (e.g., a cannula in the patient's abdomen) are removably coupled to the distal end of a manipulator 112, with the surgical instrument 120 inserted through the entry guide 124. Teleoperated actuators in the manipulator 112 move the surgical instrument 120 as a whole. The manipulator 112 further includes an instrument carriage 130. The surgical instrument 120 is detachably connected to the carriage 130. The teleoperated actuators housed in the carriage 130 provide a number of controller motions which the surgical instrument 120 translates into a variety of movements of the end effector on the surgical instrument. Thus the teleoperated actuators in the carriage 130 move only one or more components of the surgical instrument 120 rather than the instrument as a whole. Inputs to control either the instrument as a whole or the instrument's components are such that the input provided by a surgeon to the control system portion (a "master" command) is translated into a corresponding action by the surgical instrument (a "slave" response).

Figure 2:
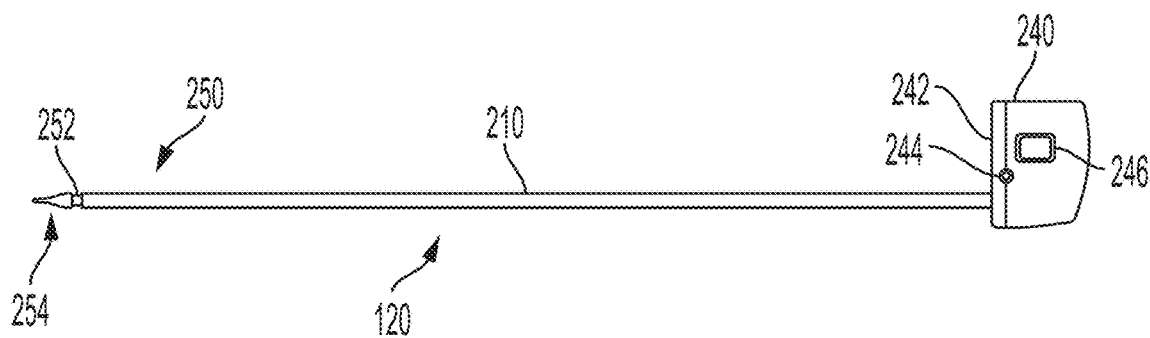
FIG. 2 is a plan view of a surgical instrument for use with an actuator.

FIG. 2 is a side view of an illustrative embodiment of the surgical instrument 120, comprising a distal portion 250 and a proximal control mechanism 240 coupled by an elongate tube 210. The distal portion 250 of the surgical instrument 120 may provide any of a variety of end effectors such as the forceps 254 shown, a needle driver, a cautery device, a cutting tool, an imaging device (e.g., an endoscope or ultrasound probe), or a combined device that includes a combination of two or more various tools and imaging devices. In the embodiment shown, the end effector 254 is coupled to the elongate tube 210 by a "wrist" 252 that allows the orientation of the end effector to be manipulated with reference to the instrument tube 210.

Teleoperated actuator controlled surgical instruments that are used with the invention are controlled by a plurality of flexible cables. Cables provide a means of transmitting forces to the joints that is compact and flexible. A typical elongate tube 210 for a surgical instrument 120 is small, perhaps six millimeters in diameter, roughly the diameter of a large soda straw. The diminutive scale of the mechanisms in the surgical instrument 120 creates unique mechanical conditions and issues with the construction of these mechanisms that are unlike those found in similar mechanisms constructed at a larger scale because forces and strengths of materials do not scale at the same rate as the size of the mechanisms. The cables must fit within the elongate tube 210 and be able to bend as they pass through the joints 252, 254 that offset the surgical tool 262.

The cables are stranded to provide flexibility. They are operated at high levels of stress and bend around pulleys of small diameters. These conditions require the actuator controlled surgical instrument to be retired after a certain number of uses. The actuator controlled surgical instrument is provided with a visual indicator 244 that may be set by an actuator when the surgical instrument has reached the rated number of uses. This alerts personnel that the surgical instrument can no longer be used and, therefore, should not be cleaned and returned to inventory.

The surgical instrument may be identified by the surgical system and the uses of the instrument tracked by the system. The visual indicator 244 may be set by the system as an aid to the personnel handling the actuator controlled surgical instrument. The visual indicator 244 setting may or may not be used by the system to determine if an actuator controlled surgical instrument is usable. The surgical instrument may or may not track the number of times it has been and set the visual indicator 244 autonomously.

Figure 3:
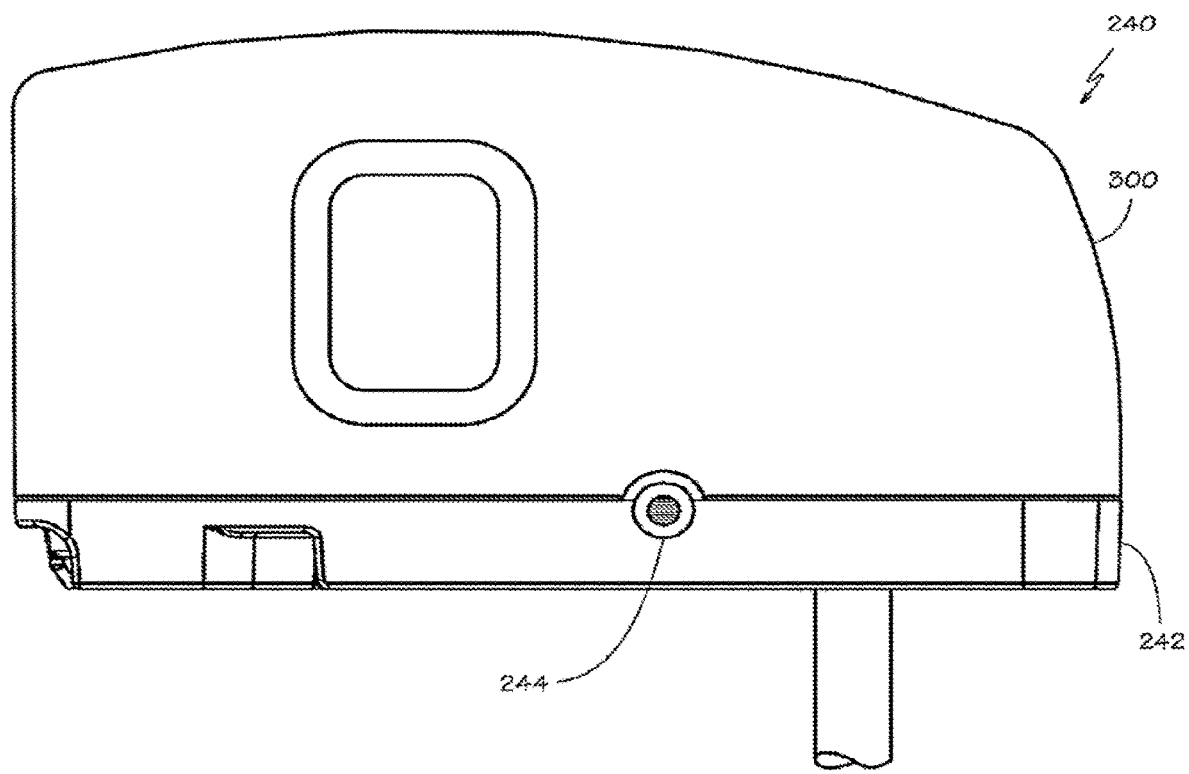
FIG. 3 is a detailed view of the proximal control mechanism 240 of the surgical instrument shown in FIG. 2.

FIG. 3 is a detailed view of the proximal control mechanism 240 of the actuator controlled surgical instrument shown in FIG. 2. In this view the visual indicator 244 may be seen more clearly. A shaded indication is illustrated to suggest an expired indication such as a red color being shown as the visual indication.

Figure 4:
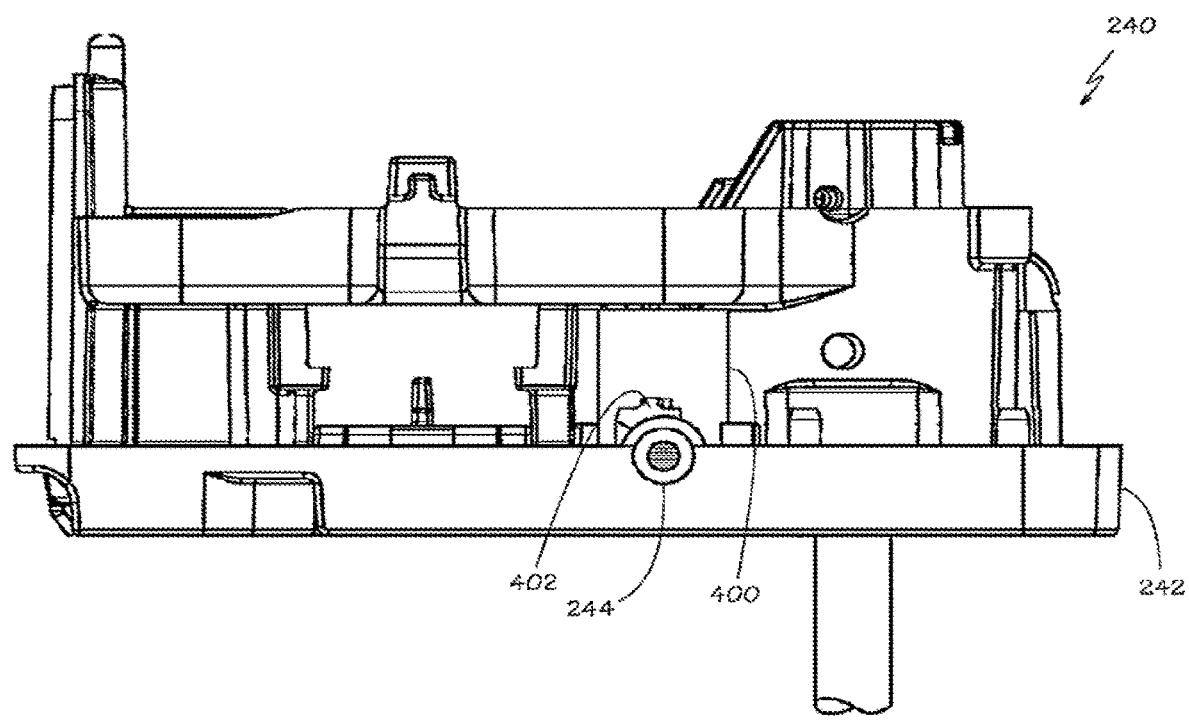
FIG. 4 is a view of the proximal control mechanism shown in FIG. 3 with the outer housing removed.

FIG. 4 is a view of the proximal control mechanism 240 shown in FIG. 3 with the outer housing 300 removed to show the indicator mechanism. The indicator may include a rotatable indicator body, such as a rotatable drum 400, that may support an indicator arm 402. The indicator arm may provide areas that are visible through an aperture to provide the visual indicator 244. In other embodiments, the areas that are visible through the aperture may be on the indicator body rather than on an indicator arm. The indicator arm is used if the distance between the axis of rotation of the indicator body and the aperture of the visual indicator 244 is such that using an indicator body alone would be too bulky.

Figure 5:
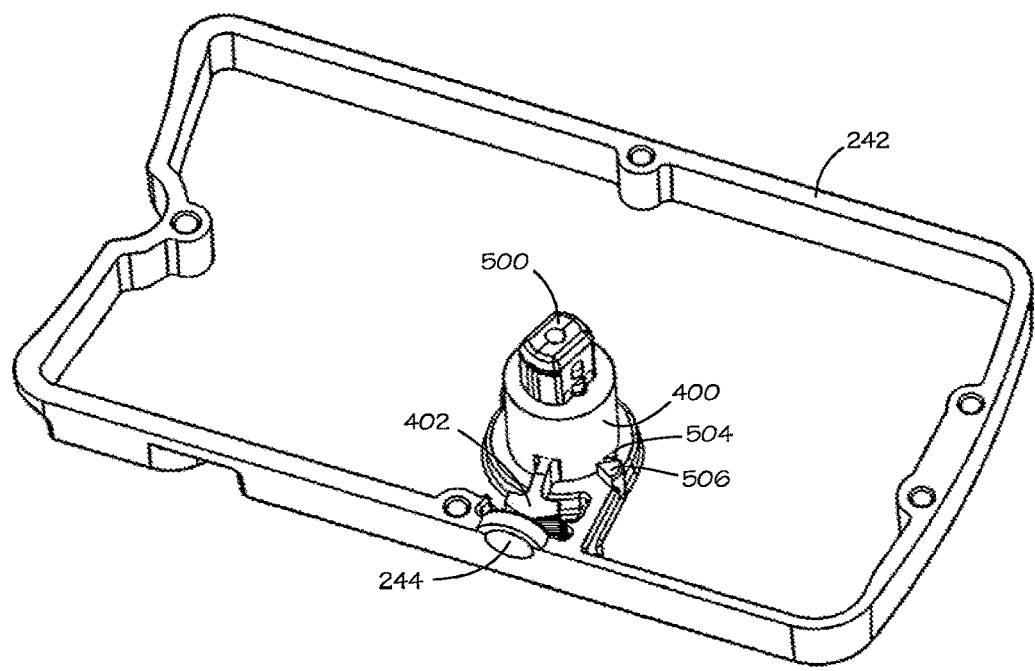
FIG. 5 is a perspective view of the proximal control mechanism shown in FIG. 4.
Figure 6:
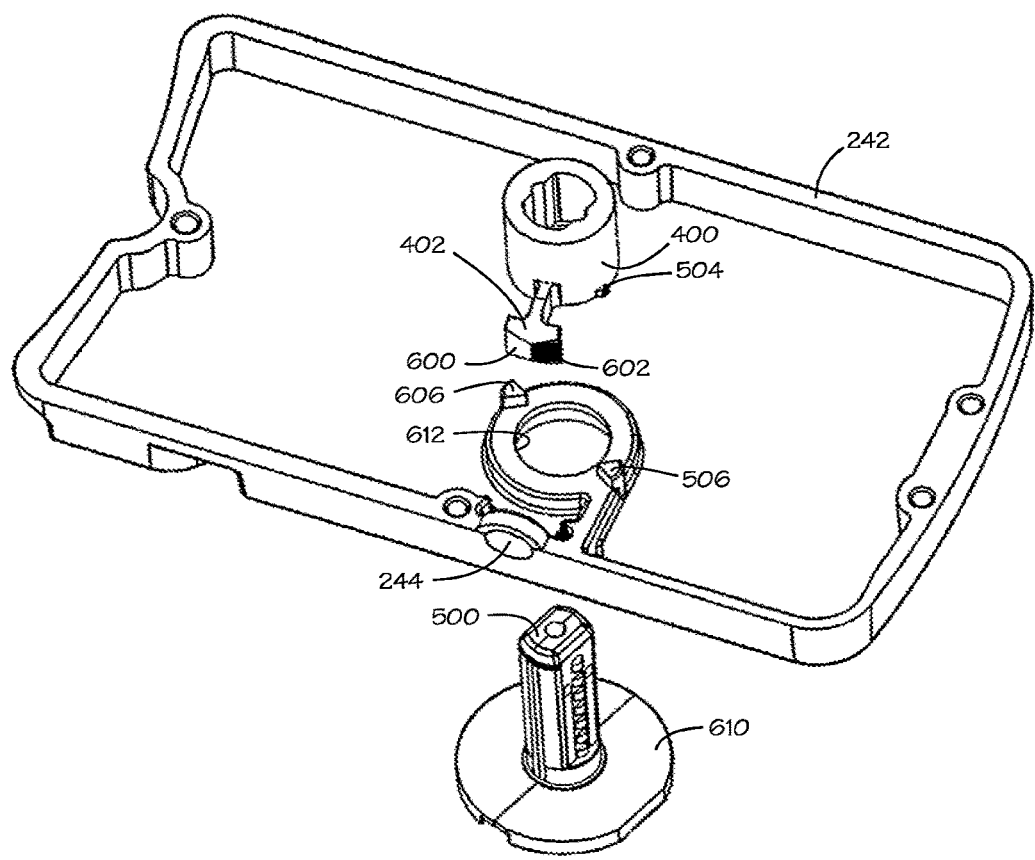
FIG. 6 is an exploded view of the proximal control mechanism.

FIG. 5 is a perspective view of the proximal control mechanism 240 shown in FIG. 4 with only the components of the indicator mechanism shown. FIG. 6 is an exploded view of the proximal control mechanism 240 which shows certain aspects of the indicator mechanism more clearly.

The rotatable drum 400 is supported by the base 242 of the proximal control mechanism. A keyed shaft 500 engages the drum 400 to rotate the drum. A driver disk 610 is provided at the end of the keyed shaft 500 that extends from the side of the base 242 opposite the side that supports the drum 400. The drum is fixed to the keyed shaft 500 such that the drum, shaft, and driver disk provide a rotatable assembly on the base 242 of the proximal control mechanism.

The areas that are visible through the aperture of the visual indicator 244 can be seen in FIG. 6. A first area 600 provides the visual indication of an instrument that is still in service. A second area 602 provides the visual indication of an instrument that has expired.

Figure 7:
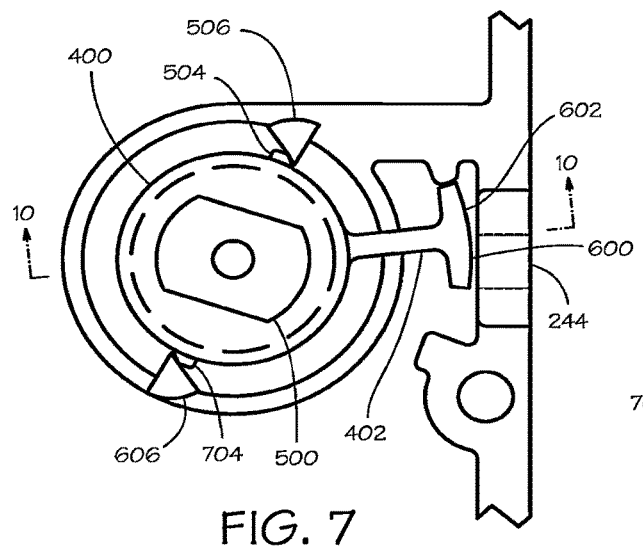
FIG. 7 is a plan view of the indicator mechanism in a first operating position.
Figure 8:
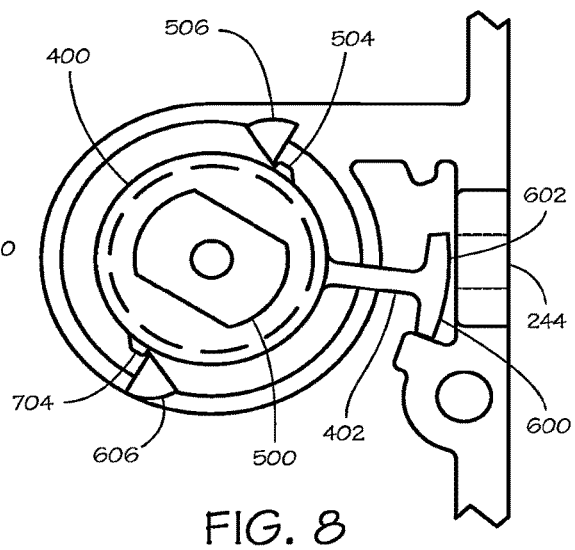
FIG. 8 is a plan view of the indicator mechanism in a second operating position.
Figure 9:
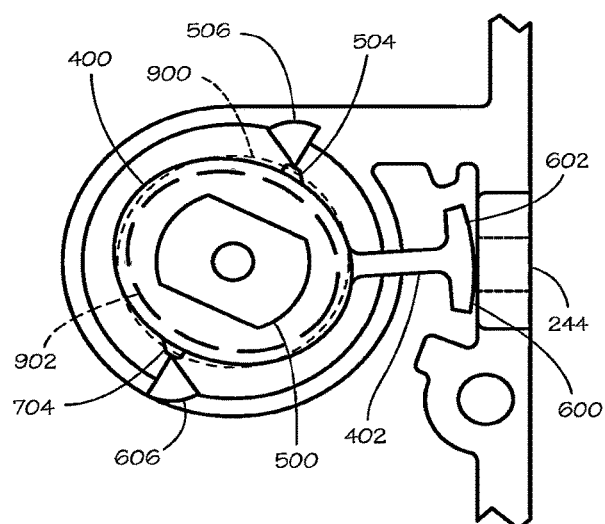
FIG. 9 is a plan view of the indicator mechanism in transition between the first and second operating positions.

FIGS. 7, 8, and 9 are plan views of the indicator mechanism in various operating positions. FIG. 7 shows the drum 400 in a first position where the first area 600 is aligned with the aperture of the visual indicator 244 to provide the visual indication of an instrument that is still in service, i.e. the instrument is usable for at least one more service cycle. FIG. 8 shows the drum 400 in a second position where the second area 602 is aligned with the aperture of the visual indicator 244 to provide the visual indication of an instrument that has expired, i.e. the instrument is not usable for an additional service cycle.

It is desirable that the drum 400 be held in either the first or second position so that the visual indicator 244 provides an unambiguous indication of the condition of the surgical instrument. It is also desirable that the drum be held securely so that the visual indicator 244 will not be moved by handling that may include vigorous cleaning activities. In some embodiments, the visual indicator may provide more than two positions and, in these embodiments, it may be desirable to hold the drum in these additional positions.

To hold the drum 400 in either the first or second position the base 242 includes detents 506, 606 that engage protrusions 504, 704 on the lower periphery of the drum adjacent the base. As illustrated in FIG. 9, the lower periphery of the drum elastically deforms when the protrusions 504, 704 are rotated past the detents 506, 606. The dashed reference circle 900 shows the undeformed outline of the drum. For clarity, the entire drum has been shown as being deformed. In reality, only the lower periphery of the drum would be deformed as shown.

While the detent mechanism has been shown as two interfering protrusions, it will be appreciated that the detent mechanism may be provided in other forms. For example, the first portion of the detent mechanism represented by the rigid detents 506, 606 on the base 242, might be provided as recesses rather than as protrusions. Likewise, the second portion of the detent mechanism represented by the elastic protrusions 504, 704 on the drum 400, might be provided as recesses rather than protrusions. In other embodiments, the first portion of the detent mechanism supported by the base 242 might be elastic while the portion supported by the drum 400 is rigid. In other embodiments, the detent mechanism may provide more than two held positions.

Figure 10:
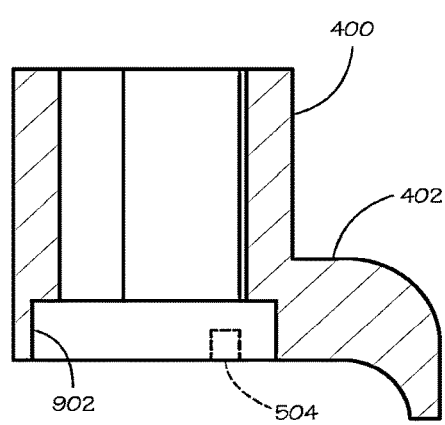
FIG. 10 is a cross-section view of the drum taken along line 10-10 in FIG. 7.

FIG. 10 is a cross-section view of the drum 400 taken along line 10-10 in FIG. 7. This shows the skirt portion 902 of the drum 400 which provides a thin section adjacent the lower periphery of the drum that can be elastically deformed to permit the protrusions 504, 704 are rotated past the detents 506, 606. As shown, the skirt portion 902 is somewhat higher than the protrusions 604 since the upper edge of the skirt portion that adjoins the full thickness portion of the drum is relatively inelastic. The thickness and the height of the skirt portion 902 may be chosen to provide a desired resistance to moving the drum from the first position to the second position.

It may be noted the protrusions 504, 704 have a sloped edge that rests against the detents 506, 606 when the drum 400 is in the first position and a square edge that rests against the detents when the drum is in the second position. Thus the protrusions provide a ratchet that allows the drum to rotate from the first position to the second and resists rotation from the second position to the first.

Figure 11:
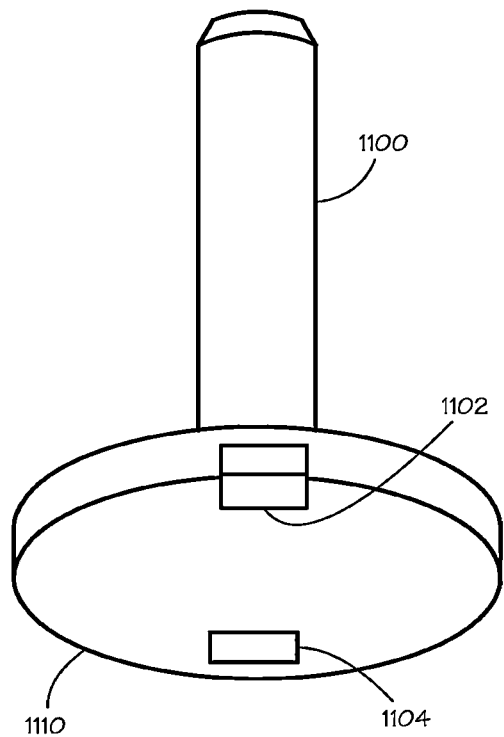
FIG. 11 is a perspective view of a keyed shaft and disk.

FIG. 11 is a perspective view of a keyed shaft 1100 and disk 1110 that may be used to rotate the drum 400 of the indicator mechanism. The disk 1110 may include recesses 1102, 1104 that engage corresponding protrusions that are driven by a motor to rotate the drum from the first position to the second position to indicate that the instrument has expired.

Figure 12:
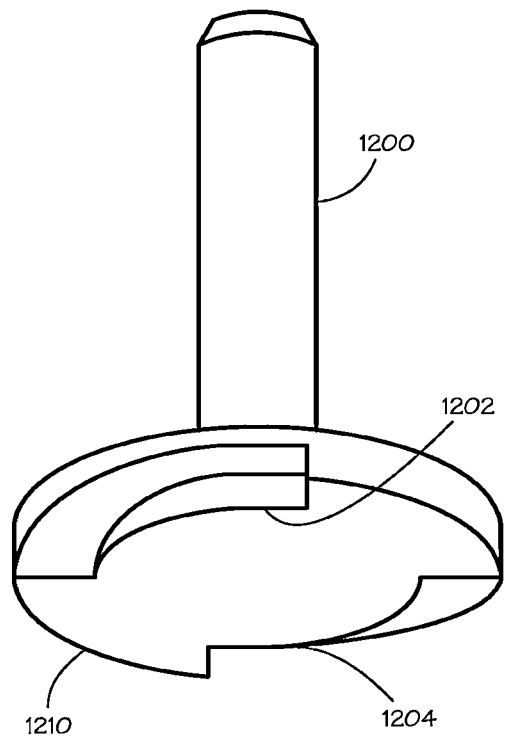
FIG. 12 is a perspective view of another keyed shaft and disk.

FIG. 12 is a perspective view of another keyed shaft 1200 and disk 1210 that may be used to rotate the drum 400 of the indicator mechanism. The disk 1210 may include recesses 1202, 1204 that engage corresponding protrusions that are driven by a motor to rotate the drum from the first position to the second position to indicate that the instrument has expired. In this embodiment, one side of each recess provides a ramp portion. This configuration allows spring loaded protrusions to reliably engage the squared side of the recess so that the motor can strike the squared side with some momentum to provide the force necessary to elastically deform the drum 400. The motor may engage the squared side slowly with a low force to establish the position of the squared side and then back up a known amount before striking the squared side at high speed. In another embodiment, positions of the motor and the squared sides are known to the motor controller. The motor controller may position the motor to place the engaging protrusions away from the squared sides based on the known positions.

Figure 13:
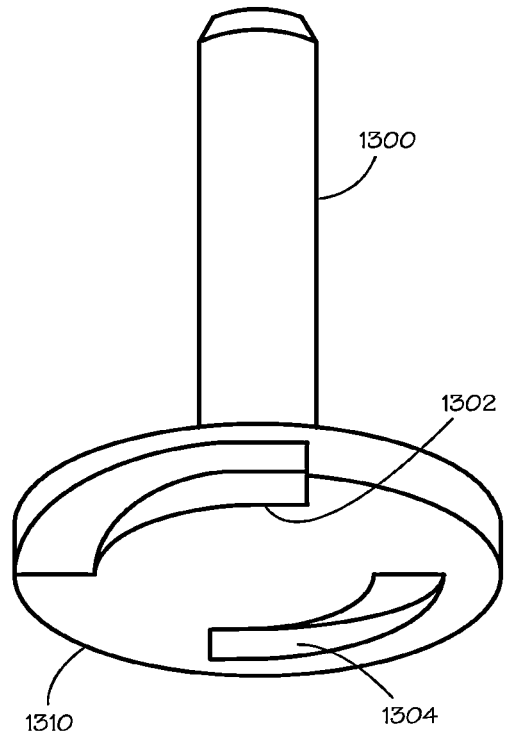
FIG. 13 is a perspective view of still another keyed shaft and disk.

FIG. 13 is a perspective view of still another keyed shaft 1300 and disk 1310 that may be used to rotate the drum 400 of the indicator mechanism. This embodiment provides ramped recesses 1302, 1304 similar to those shown in FIG. 12. However, the recesses are at different distances from the axis of rotation of the shaft 1300 and drum 400. This allows the protrusions to be rotated almost one full revolution before striking the squared sides of the recesses which may allow a greater force to be delivered to rotate the drum from the first position to the second position to indicate that the instrument has expired.

It will be appreciated that the keyed shaft and disk could provide protrusions that engage corresponding recesses that are driven by a motor and that the recesses could have forms similar to those shown for the disk portion of the keyed shaft.

Figure 14A:
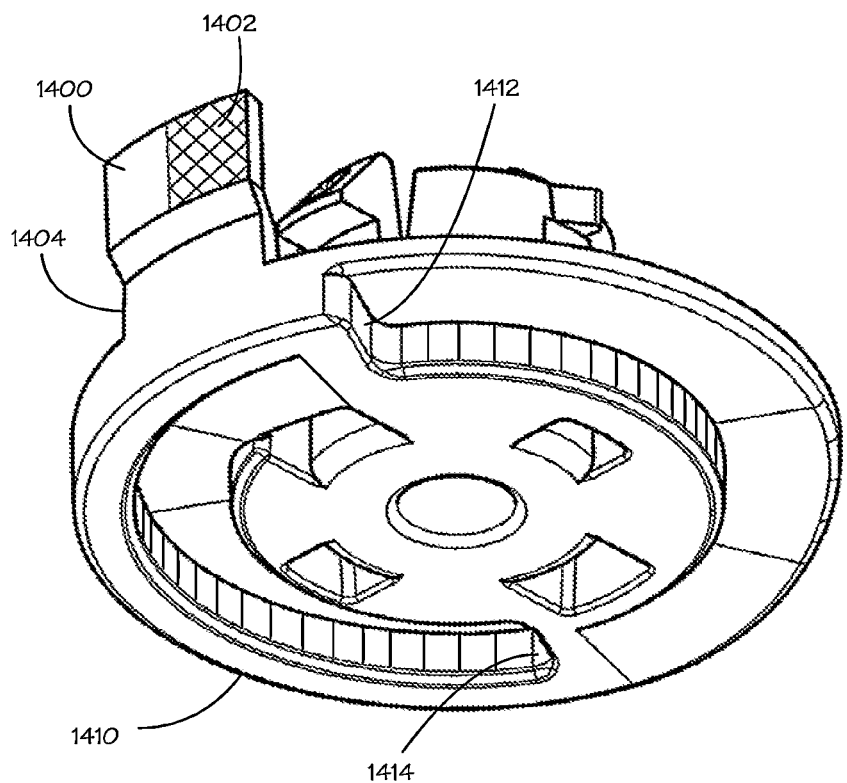
FIGS. 14A and 14B are perspective views of two sides of another embodiment of the indicator mechanism.
Figure 14B:
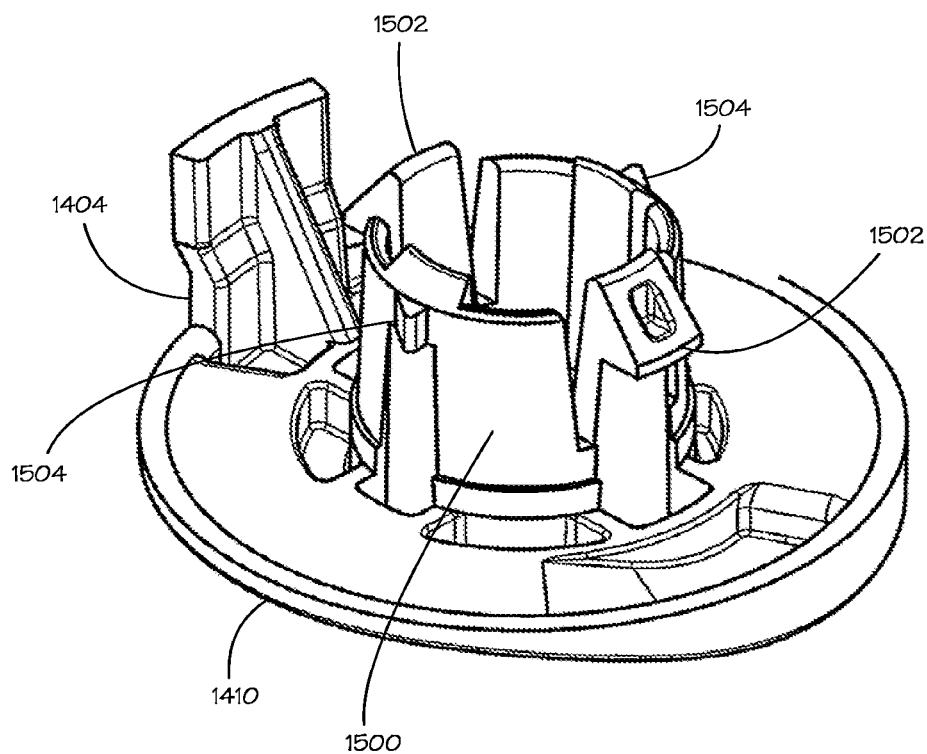

FIGS. 14A and 14B show perspective views of two sides of another embodiment of the indicator mechanism. This embodiment provides an indicator body in the form of a disk 1410 and an indicator arm 1404 in a single part. The disk includes features, such as ramps with squared sides 1412, 1414, for engaging a motor that rotates the disk. The indicator arm extends from the periphery of the disk parallel to the axis of rotation of the disk.

A shaft 1500 extends from the disk 1410. The shaft is inserted into the opening 612 seen in FIG. 6. Hook features 1502 engage the surface of the base 242 of the proximal control mechanism on the side furthest from the disk. Protrusions 1504 on the shaft 1500 engage the detents 506, 606 on the base 242 and operate as previously described.

An additional opening is provided in the base 242 of the proximal control mechanism to allow the indicator arm 1404 to extend into the interior of the proximal control mechanism. This allows the end of the indicator arm furthest from the disk to be seen through the aperture of the visual indicator 244. The end of the indicator arm may be decorated with two visually distinct areas 1400, 1402 to provide the visual indication of whether or not the instrument has expired.

In another embodiment, the indicator arm is visible through the aperture of the visual indicator 244 in one state, such as when the instrument is still in service. In the second state, such as when the instrument has expired, the indicator arm is not visible through the aperture of the visual indicator 244. In the second state a visual feature on the base that is occluded by the indicator arm in the first state becomes visible to provide the visual indication of the second state.

Figure 15:
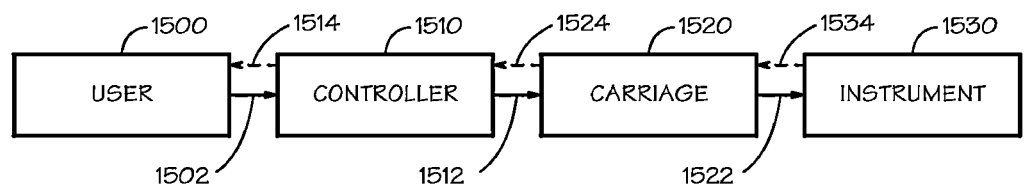
FIG. 15 is a block diagram showing a control system that may be used with a surgical instrument that includes a mechanism for displaying a visual indication of the expiration of the surgical instrument.

FIG. 15 is a block diagram showing a control system that may be used with a surgical instrument 1530 that includes a mechanism for displaying a visual indication of the expiration of the surgical instrument, As described above, the surgical instrument 1530 may be coupled to an instrument carriage 1520 that provides mechanical and/or electrical inputs 1522 that actuate and control the surgical instrument. A controller 1510 may provide inputs 1512 to the instrument carriage 1520, typically electrical inputs, to control the operations of the instrument carriage.

The surgical instrument 1530 may provide mechanical and/or electrical outputs 1534 to indicate conditions at the surgical instrument. The instrument carriage 1520 may provide outputs 1524, typically electrical outputs, to pass through the outputs 1534 from the surgical instrument and/or indicate conditions at the instrument carriage. The controller 1510 may provide outputs 1514 to the user 1500 to provide indications of various conditions of the surgical instrument 1530 and/or the surgical system.

Figure 16:
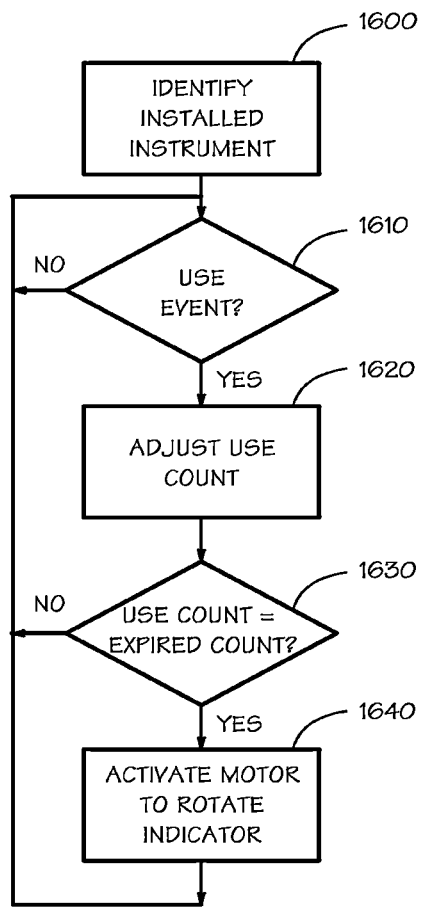
FIG. 16 is a flowchart of a method that may be performed by the controller for providing a visual indication of whether or not the surgical instrument 1530 is expired.

FIG. 16 is a flowchart of a method that may be performed by the controller 1510 for providing a visual indication of whether or not the surgical instrument 1530 is expired. The surgical instrument 1530 includes an indicator mechanism of any of the types described above. The surgical instrument 1530 also includes a mechanism, such as an RFID tag, that allows the controller 1510 to identify the particular surgical instrument that is installed 1600. Identification of the surgical instrument 1530 allows the controller to maintain the usage history for the particular surgical instrument and to identify the type and amount of usage that causes the surgical instrument to be expired.

The controller determines if a use event has occurred 1610—YES. While the flowchart shows the detection of a use event 1610 as a polling loop, it will be understood that the occurrence of a use event may be used to direct the method without the need for polling.

Some surgical instruments may expire after being used for a predetermined number of surgical procedures. For such a surgical instrument a use event may be the installation of the surgical instrument. Since a surgical instrument may be removed and reinstalled during the course of a single surgical procedure, a use event may be the installation of the surgical instrument after a predetermined length of time since the previous installation of the surgical instrument. A use event may also be the installation of the surgical instrument after a system power cycle has occurred since the previous installation of the surgical instrument.

Other surgical instruments may expire after a predetermined number of actuations of the surgical instrument. For example, a surgical stapler may allow a predetermined number of firings. Surgical shears may allow a predetermined number of closings. For such surgical instruments, the controller will identify the appropriate actuations of the surgical instrument as use event.

When a use event occurs 1610—YES, the controller 1510 will adjust a use count 1620 for the particular surgical instrument 1530 that has been identified as being installed 1600. The controller 1510 then compares the use count to a predetermined expired count to determine if the particular surgical instrument 1530 has expired 1630. It will be appreciated that the controller may accumulate the use count and compare it to the predetermined expired count or it may set the use count to the predetermined expired count and decrement the use count so that a zero value of the use count indicates that the particular surgical instrument 1530 has expired 1630.

When the controller 1510 determines that the particular surgical instrument 1530 has expired 1630—YES, the controller provides an output 1512 to the instrument carriage 1520 that activates a motor to rotate an indicator body in the surgical instrument from a first position to a second position to provide a visual indication on the surgical instrument that the surgical instrument has expired. The controller 1510 may issue commands to the instrument carriage 1520 to rotate the motor in a way that allows the motor to gain momentum before rotating the indicator body. This may enable the motor to overcome the resistance of mechanisms provided to prevent accidental rotation of the indicator body.

It will be appreciated that other criteria may be used to identify a use event in addition to those described as examples. In some cases use events are such that it would not be possible for a mechanism wholly contained in the surgical instrument to determine when the surgical instrument has expired. The method of providing a visual indication of whether or not the surgical instrument is expired described here allows other system conditions and events to be considered to determine when the surgical instrument has expired.

While certain exemplary embodiments have been described and shown in the accompanying drawings, it is to be understood that such embodiments are merely illustrative of and not restrictive on the broad invention, and that this invention is not limited to the specific constructions and arrangements shown and described, since various other modifications may occur to those of ordinary skill in the art. The description is thus to be regarded as illustrative instead of limiting.

What is claimed is:

1. An indicator mechanism for a surgical instrument, the indicator mechanism comprising:
    a base;
    an aperture defined in the base;
    a rotatable driver disk coupled to the base, wherein the rotatable driver disk is configured to be driven by a motorized actuation force;
    a visual indicator coupled to the rotatable driver disk, the visual indicator being visible through the aperture; and
    a detent mechanism configured to hold the rotatable driver disk in differing rotational positions, the detent mechanism comprising:
        one or more first detent features on an elastically deflectable member coupled to the rotatable driver disk, and
        one or more second detent features on the base and configured to engage the one or more first detent features, wherein engagement of the one or more first detent features with the one or more second detent features holds the rotatable driver disk in respective rotational positions of the differing rotational positions.

2. The indicator mechanism of claim 1, wherein differing regions of the visual indicator are displayed through the aperture based on the differing rotational positions in which the rotatable driver disk is held by the detent mechanism and wherein the differing regions provide differing visual indications that convey information about a life of the surgical instrument.

3. The indicator mechanism of claim 1, wherein the rotatable driver disk is configured to be driven by the motorized actuation force output by an instrument manipulator.

4. The indicator mechanism of claim 1, wherein the elastically deflectable member is configured to deflect in response to actuation of driven rotation of the rotatable driver disk so as to enable release of the one or more first detent features from the one or more second detent features.

5. The indicator mechanism of claim 1,
wherein the rotatable driver disk is located at a first side of the base,
wherein the visual indicator is located at a second side of the base opposite the first side, and
wherein the base is configured to engage with a housing covering the second side of the base.

6. The indicator mechanism of claim 1, further comprising a drum, wherein the elastically deflectable member is a relatively thin-walled portion of the drum.

7. The indicator mechanism of claim 6, further comprising a shaft coupled to the rotatable driver disk, wherein the drum receives and is coupled to the shaft.

8. The indicator mechanism of claim 6, wherein the elastically deflectable member is configured to deflect in response to actuation of driven rotation of the rotatable driver disk so as to enable release of the one or more first detent features from the one or more second detent features.

9. The indicator mechanism of claim 6, further comprising an arm extending radially outwardly from the drum, wherein the visual indicator is at a free end of the arm.

10. The indicator mechanism of claim 1, wherein the elastically deflectable member comprises one or more portions of a shaft extending from the rotatable driver disk.

11. The indicator mechanism of claim 10, wherein the shaft is hollow.

12. The indicator mechanism of claim 10, further comprising an arm extending in an axial direction from the rotatable driver disk, wherein the visual indicator is at a free end portion of the arm.

13. The indicator mechanism of claim 10, wherein the elastically deflectable member is configured to deflect in response to actuation of driven rotation of the rotatable driver disk so as to enable release of the one or more first detent features from the one or more second detent features.

14. An instrument comprising:
a shaft extending between a proximal end portion and a distal end portion;
an end effector coupled to the distal end portion of the shaft;
a control mechanism coupled to a proximal end portion of the shaft and configured to transmit force to control the end effector, wherein the control mechanism comprises:
a base,
a housing coupled to the base,
an aperture defined in the base,
a rotatable driver disk coupled to the base, wherein the rotatable driver disk is configured to be driven by a motorized actuation force,
a visual indicator coupled to the rotatable driver disk, the visual indicator being covered by the housing and visible through the aperture, and
a detent mechanism configured to hold the rotatable driver disk in differing rotational positions, the detent mechanism comprising:
one or more first detent features on an elastically deflectable member coupled to the rotatable driver disk, and
one or more second detent features on the base and configured to engage the one or more first detent features, wherein engagement of the one or more first detent features with the one or more second detent features holds the rotatable driver disk in respective rotational positions of the differing rotational positions.

15. The instrument of claim 14, further comprising a drum, wherein the elastically deflectable member is a relatively thin-walled portion of the drum.

16. The instrument of claim 14, wherein the elastically deflectable member is configured to deflect in response to actuation of driven rotation of the rotatable driver disk so as to enable release of the one or more first detent features from the one or more second detent features.

17. The instrument of claim 14, wherein the shaft is a first shaft and the elastically deflectable member comprises one or more portions of a second shaft extending from the rotatable driver disk.

18. The instrument of claim 14, wherein differing regions of the visual indicator are displayed through the aperture based on the differing rotational positions in which the rotatable driver disk is held by the detent mechanism and wherein the differing regions provide differing visual indications that convey information about a life of the instrument.

19. The instrument of claim 14, wherein the control mechanism is configured to removably couple with an instrument manipulator, and wherein the rotatable driver disk is configured to driven by a motorized actuation force output by the instrument manipulator in a coupled state of the control mechanism with the instrument manipulator.

* * * * *